(12) United States Patent
Fischer, Jr. et al.

(10) Patent No.: US 6,906,857 B2
(45) Date of Patent: Jun. 14, 2005

(54) OPTICAL FILTERS FOR MANIPULATING SPECTRAL POWER DISTRIBUTION IN ACCELERATED WEATHERING DEVICES

(75) Inventors: Richard M. Fischer, Jr., Hudson, WI (US); Bradley D. Guth, Hudson, WI (US); Warren D. Ketola, St. Paul, MN (US); James W. Riley, Inver Grove Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/802,430

(22) Filed: Mar. 17, 2004

(65) Prior Publication Data

US 2004/0178367 A1 Sep. 16, 2004

Related U.S. Application Data

(62) Division of application No. 10/028,601, filed on Dec. 19, 2001, now Pat. No. 6,859,309.

(51) Int. Cl.$^7$ .............................................. G02B 13/14
(52) U.S. Cl. ..................... 359/350; 359/355; 359/359
(58) Field of Search ................................ 359/350, 355, 359/359, 361, 356; 65/378, 485; 250/492.1, 492.2, 493.1, 504 R, 503.1, 505.1; 73/856.6

(56) References Cited

U.S. PATENT DOCUMENTS

| | | | |
|---|---|---|---|
| 4,820,326 A | 4/1989 | Speit | |
| 4,859,903 A | 8/1989 | Minematu et al. | |
| 4,931,655 A | 6/1990 | Yoshida et al. | |
| 6,108,126 A | 8/2000 | Hagiwara et al. | |
| 6,225,244 B1 | 5/2001 | Oguma | |

FOREIGN PATENT DOCUMENTS

| | | |
|---|---|---|
| DE | 29 40 325 | 9/1981 |
| DE | 35 04 793 | 8/1986 |
| DE | 19736189 | 2/1999 |
| JP | H2-188442 | 7/1990 |
| JP | 3252604 | 11/1991 |
| JP | 9306201 | 11/1997 |
| SU | 539344 | 12/1976 |
| SU | 1067412 | 4/1984 |

OTHER PUBLICATIONS

Sayre et al.; "Discrepancies in the Measurement of Spectral Sources"; Photochemistry and Photobiology, vol. 55, No. 1, pp. 141–143; 1992.
Powell; "D65 simulation with a xenon arc"; Applied Optics, vol. 35, No. 34, Dec. 1, 1996; pp. 6708–6713.

*Primary Examiner*—Drew A. Dunn
*Assistant Examiner*—Joshua L. Pritchett
(74) *Attorney, Agent, or Firm*—Carolyn A. Fischer

(57) ABSTRACT

The present disclosure is directed to an optical filter that advantageously approximates sunlight that is both durable and stable for long periods of time when subject to harsh light intensity, thermal and moisture loads of accelerating weathering devices. The optical filter includes a glass having a lead content of between 0.5% and 50% by weight. In some examples, the filter can be constructed to have a thickness of 0.7 mm to 10 mm. In another aspect of the disclosure, the optical filter is part of an optical filter assembly suitable for manipulating spectral power distribution. The optical filter assembly includes a lead glass optical filter having a lead content of between 0.5% and 50% by weight and an ultraviolet transmissive optical filter. In one example, the ultraviolet transmissive optical filter is constructed from quartz glass. The ultraviolet transmissive optical filter can further include an infrared absorbing coating. In still another aspect of the present disclosure, an optical filter constructed from a lead glass has a thickness selected such that illumination passed through the lead glass has a first ratio and a second ratio. The first ratio is a first total irradiance for wavelengths shorter than 290 nm to a second total irradiance for wavelengths between 300 nm to 400 nm, such that the first ratio is less than $2.0 \times 10^{-6}$. The second ratio is an irradiance at 310 nm to the second total irradiance, wherein the second ratio is at least $1.2 \times 10^{-3}$.

17 Claims, 6 Drawing Sheets

OPTICAL FILTERS FOR MANIPULATING SPECTRAL POWER DISTRIBUTION IN ACCELERATED WEATHERING DEVICES

RELATED APPLICATIONS

This application is a divisional application of U.S. application Ser. No. 10/028,601 filed Dec. 19, 2001, now U.S. Pat. No. 6,859,309.

BACKGROUND

Accelerated weathering devices are used by a number of industries to test a product's resistance to outdoor environments. Often, a manufacturer of a given product will ensure that the product will endure outdoor weather for a specified lifetime. The product must be able to withstand temperature cycles, moisture stresses such as humidity, condensation, and rain, as well as exposure to terrestrial solar radiation. These are important stresses for producing degradation of products used outdoors, and simulation of these stresses is essential for devices that are used for laboratory accelerated weathering tests. Although all three stresses act to produce degradation, exposure to solar radiation is one of the more influential factors in weathering because ultraviolet rays generally tend to break down polymers and other materials over time.

Accelerated weathering devices using an artificial light source have advantages because the use of the devices is not subject to climatic and seasonal variations of temperature, moisture, and terrestrial solar radiation. Among the more difficult tasks in the manufacture of accelerated weathering devices is to provide a spectral power distribution in the artificial light that matches closely to that of natural sunlight on earth. By matching or closely approximating the spectral power distribution of natural sunlight, the results of exposure to the accelerated weathering device will more closely approximate effects of real world exposure.

Approximating spectral power of sunlight is typically accomplished by passing illumination from the artificial light source through one or more optical filters. If this approximating is not done effectively, failure modes observed experimentally in products under test may not match real world failures. Wavelengths of light that are present in artificial light when passed through optical filters and not present in terrestrial sunlight have been found to change the balance of degradation and stabilization reactions. To the extent possible, these wavelengths of light should be eliminated from test protocols. Typical optical filters for accelerated weathering devices, as demonstrated with respect to the comparative examples, pass illumination that does not advantageously approximate sunlight. For example, many filters pass more amounts of ultraviolet radiation at wavelengths less than 290 nm than in actual terrestrial solar radiation, which has only very small amounts of radiation at wavelengths less than 290 nm. Radiation at these wavelengths can cause some materials to fail prematurely, such as polyethylene terpthalate and polyurethanes with phthalate containing polyols. In addition, many filters that do not pass this short wavelength radiation also insufficiently transmit light within the solar spectrum, particularly light at or about 310 nm and can lead to slower degradation rates or longer test times.

To compound the difficulty of manufacturing a suitable optical filter, the optical filters used in accelerated weathering devices are subject to harsh light intensity, thermal and moisture loads. Optical filters must be durable and stable for long periods of time in harsh environments. A filter for an accelerated weathering device may not be selected simply by spectral characteristics alone. Rather, an effective optical filter for an accelerated weathering device must have spectral characteristics that match sunlight and be durable enough to withstand use in the accelerated weathering device.

A significant need exists to provide optical filters for accelerated weathering devices that allow these devices to more closely match the spectral power distribution of terrestrial solar radiation while accommodating the harsh conditions within such devices for an acceptable lifetime.

SUMMARY

The present disclosure is directed to an optical filter that advantageously approximates sunlight and that is both durable and stable for long periods of time when subject to harsh light intensity, thermal and moisture loads of accelerated weathering devices. The optical filter includes a glass having a lead content of between 0.5% and 50% by weight. In some examples, the filter can be constructed to have a thickness of 0.7 mm to 10 mm. In another aspect of the disclosure, the optical filter is part of an optical filter assembly suitable for manipulating spectral power distribution. The optical filter assembly includes a lead glass optical filter having a lead content of between 0.5% and 50% by weight and an ultraviolet transmissive optical filter. In one example, the ultraviolet transmissive optical filter is constructed from quartz glass. The ultraviolet transmissive optical filter can further include an infrared absorbing coating. In still another aspect of the present disclosure, an optical filter constructed from a lead glass has a thickness selected such that illumination passed through the lead glass has a first ratio and a second ratio. The first ratio is a first total irradiance for wavelengths shorter than 290 nm to a second total irradiance for wavelengths between 300 nm to 400 nm, such that the first ratio is less than $2.0 \times 10^{-6}$. The second ratio is an irradiance at 310 nm to the second total irradiance, wherein the second ratio is at least $1.2 \times 10^{-3}$.

The present disclosure describes an optical filter having several advantages. Among these advantages include an optical filter that more closely simulates sunlight than the comparative examples and is durable to withstand the harsh environments of an accelerated weathering device. Also, the cut-on wavelength of such a filter can be easily adjusted to provide a selected cut-on wavelength for testing. Additionally, the filters can operate over a wide power range and still advantageously approximate sunlight. Also, testing at typical specified irradiance levels can be conducted at lower lamp power settings.

DETAILED DESCRIPTION

Figure 1:
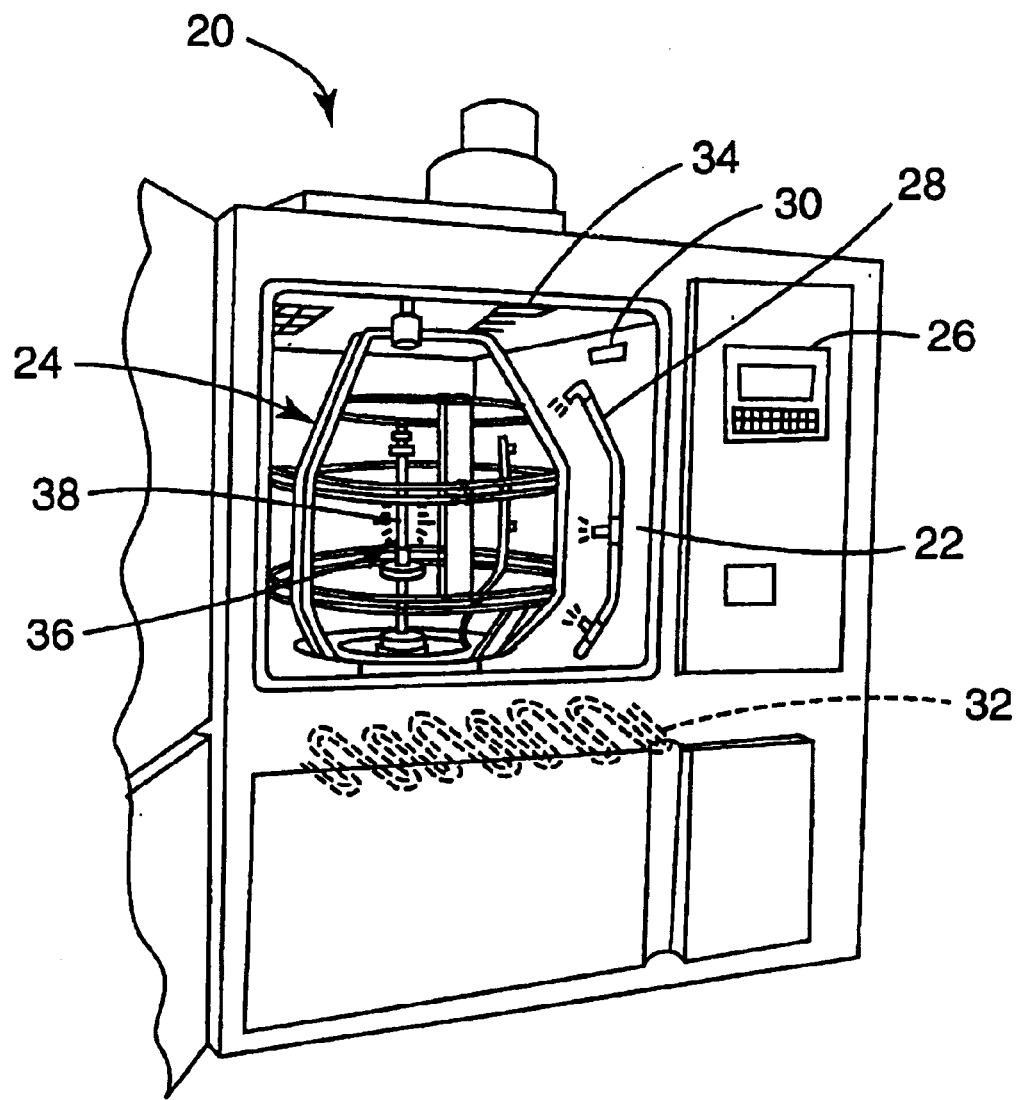
FIG. 1 shows a perspective view of an accelerated weathering device constructed in accordance with the invention.

FIG. 1 is one example of an accelerated weathering device 20. The accelerated weathering device 20 includes a weathering chamber 22. Inside the weathering chamber 22 is a weathering fixture 24 adapted to hold a number of product samples (not shown) for testing. Test parameters, in the example, are input through user-interface 26. Examples of test parameters include moisture stresses such as humidity, water spray, condensation, temperature, and irradiance. Mist generators 28 provide atomized water into the weathering chamber 22. Humidity within the chamber is measured via humidity sensor 30. Heater 32 generates heat within the chamber 22. Heat is measured with a temperature sensor 34. Signals received from the sensors 30, 34 are used to control or maintain the temperature and moisture stresses within the chamber 22. The weathering chamber 22 also includes an illumination assembly 36 which includes illuminator 38. The illumination assembly 36 provides and controls irradiance and works to cool illuminator 38. In the example shown, the illuminator 38 is disposed near the center of the weathering fixture 24 to provide irradiance to the product samples.

Figure 2:
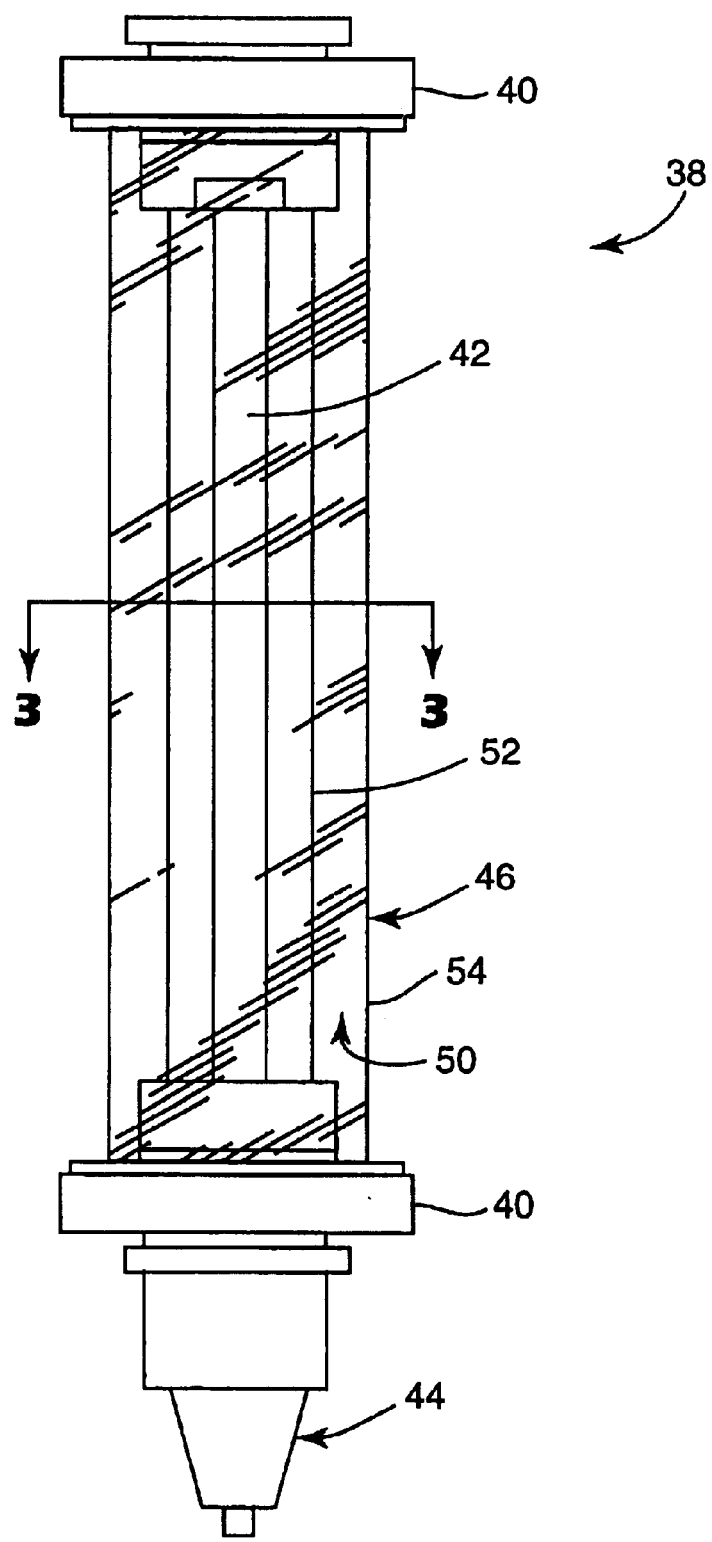
FIG. 2 shows a side view of an illuminator used within the accelerated weathering device of FIG. 1.

FIG. 2 shows one example of the illuminator 38. The illuminator 38 includes a pair of end caps 40 that couple and retain the light source 42. Plug 44 mates with a conductor in the illumination assembly 36 to provide power to the light source 42. The light source 42 is surrounded by at least one optical filter or, in the example shown, an optical filter assembly 46. An optical filter assembly is a plurality of optical filters. A coolant 50 flows through the illuminator 38 to control and maintain the temperature of the illuminator 38. Light source 42 includes a lamp having spectral emissions at least in the range of 200 nm to 400 nm. Examples of known light sources suitable for use in accelerated weathering devices include carbon-arc lamps, xenon-arc lamps, metal halide lamps, fluorescent lamps, and the like. In the examples shown, the light source 42 is a xenon-arc lamp and the fluid coolant 50 is water.

Figure 3:
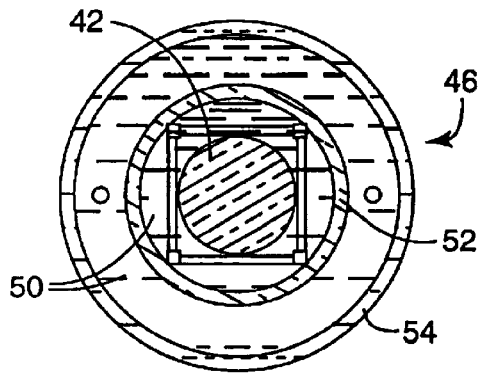
FIG. 3 shows a cross-section view of the illuminator of FIG. 2.

FIG. 3 shows a cross-section of the optical filter assembly 46 taken along line 3—3 of FIG. 2. In the example shown, the optical filter assembly 46 includes two optical filters, that is inner filter 52 and outer filter 54. The optical filters 52 and 54 are shown having a circular cross-section indicating that the filter assembly 46 is cylindrical. Other curvilinear or rectilinear shapes for the optical filters 52, 54 are contemplated. Coolant 50 flows in a first direction along the length of the illuminator 38 between the light source 42 and the inner filter 52. Coolant 50 flows in the opposite direction between the inner filter 52 and the outer filter 54. Other systems can include a cooling water inlet on one end and an outlet on the other.

Figure 4:
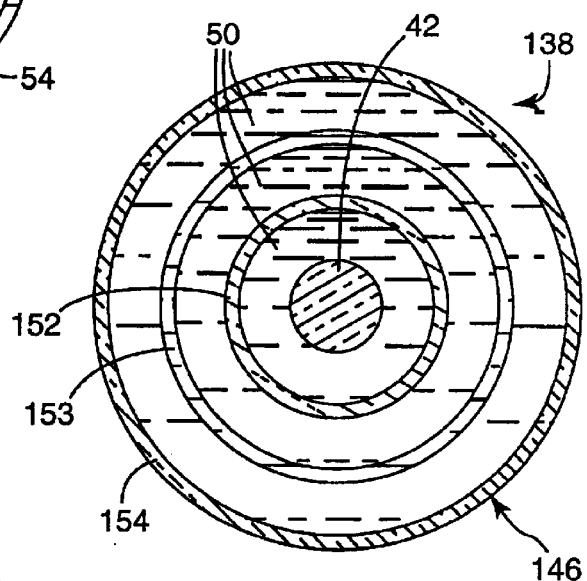
FIG. 4 shows a cross-section view of another example of an illuminator.

FIG. 4 shows a cross-section of another example of an illuminator 138 with an optical filter assembly 146, which includes three optical filters, that is inner filter 152, middle filter 153 and outer filter 154. Coolant 50 flows in a first direction along the length of the illuminator 138 between light source 42 and inner filter 152. The coolant flows in the opposite direction between both the inner filter 152 and middle filter 153 and middle filter 153 and outer filter 154.

Figure 5:
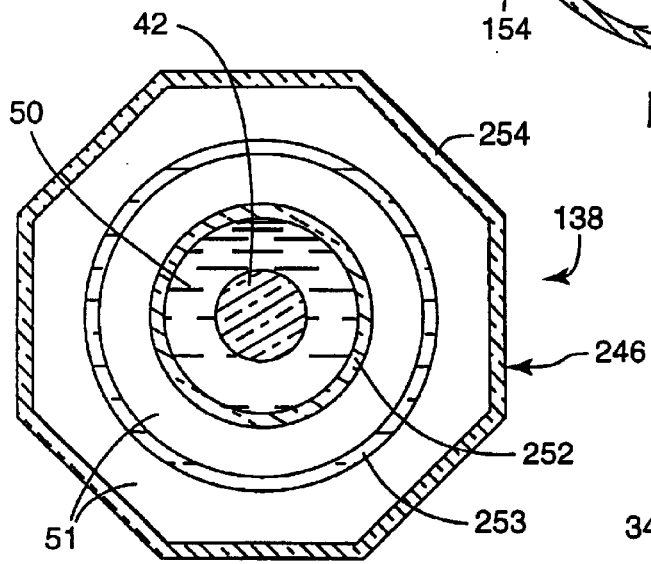
FIG. 5 shows a cross-section view of still another example of an illuminator.

FIG. 5 shows still another example of illuminator 238 with optical filter assembly 246 which includes three optical filters, that is inner filter 252, middle filter 253 and outer filter 254. In the example, a liquid coolant 50 such as water is passed in a first direction between the light source 42 and inner filter 252, and in the opposite direction between inner 252 and middle filter 253. A gaseous coolant 51 such as air is passed between the middle filter 253 and outer filter 254.

Figure 6:
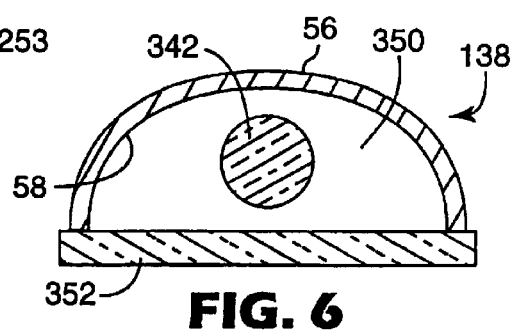
FIG. 6 shows a cross-section view of still another example of an illuminator.

FIG. 6 shows one example of an illuminator 338 which includes a single optical filter 352. In the example, the optical filter is a pane or flat filter and is connected to reflector 56 having a reflective concave surface 58. The combination of the reflector 56 and the optical filter 352 surrounds the light source 342. The illuminator 338 in the example is cooled with gaseous coolant 350 such as air. In this arrangement, the example is shown with a metal halide light source 342, although other light sources, such as xenon-arc light sources, are suitable for use in the illuminator 338. An illuminator with a single filter, rather than a plurality of filters, surrounding the light source and without a reflector is contemplated. Also, the use of a coolant other than a gaseous coolant is contemplated.

The examples shown in FIGS. 2–6 are not exhaustive of the possible examples within the scope of the claims. Illustratively, the figures show an elongated illuminator. The illuminator may take any tangible form. Additionally, optical filters in a filter assembly may be adjacent to and touching one another rather than spaced apart as shown. Illuminators may be constructed without end caps 40. Other variations are contemplated and may be imagined and still be within the scope of the appended claims.

The optical filter, or optical filter assembly, is selected to tailor illumination from the light source out of the illuminator to advantageously approximate solar radiation. Thus the illuminator provides a more realistic weathering test than with previous filters. Two spectral regions are of interest in defining how well the illuminator or filters simulate solar radiation. The first spectral region includes wavelengths shorter than 290 nm. Ultraviolet radiation less than 290 nm is high energy and causes rapid polymer degradation. Terrestrial solar ultraviolet light has very little radiation below 290 nm. The second spectral region includes irradiance at 310 nm. In general, irradiance is the radiant power per unit area incident on a receiver, typically reported in watts per square meter (W/m$^2$). As described above, terrestrial solar radiation is insignificant below 290 nm and becomes significant at about 300 nm. Thus, the solar cut-on wavelength is typically between 290 nm–300 nm at midsummer at noon. Irradiance at 310 nm provides a realistic indication about whether the filtered light has sufficient irradiance in the region just above the solar cut-on to provide an effective test.

In this disclosure, the cut-on wavelength is defined as the shortest wavelength where irradiance is at least 0.001 W/m$^2$ when tested with a xenon-arc or metal halide light source. Test methods for determining the cut-on wavelength are susceptible to noise. In order to account for noise, the cut-on wavelength can also be defined as the wavelength where the measured irradiance is the fourth in succession of increasing integer wavelength with increasing irradiance and the minimum irradiance is 0.00002 W/m$^2$.

In order to provide advantageous simulation of terrestrial solar radiation, the filter preferably is designed so as to satisfy two criteria related to the above-described spectral regions. First, illumination from the light source passing through the optical filter, or filtered illumination, has a ratio of a first total irradiance for wavelengths shorter than 290 nm to a second total irradiance for wavelengths between 300 nm and 400 nm equal to or less than 2.0×10$^6$. Second, illumination from the light source passing through the optical filter has a ratio of an irradiance at 310 nm to the second total irradiance (the total irradiance between 300 nm to 400 nm) of greater than or equal to $1.2 \times 10^{-3}$. Total irradiance is the sum of the irradiance measured for each integer wavelength over a given range. A suitable method for determining total irradiance is to make measurements of irradiance at 2 nm increments, then add up the irradiance at each measured wavelength and multiply the resulting sum by 2. To calculate the first total irradiance, the sum of the irradiance measured from 250 nm to 288 nm at 2 nm increments is multiplied by 2. To calculate the second total irradiance, the sum of the irradiance measured from 300 nm to 400 nm at 2 nm increments is multiplied by 2.

An optical filter or at least one optical filter in a filter assembly that includes a glass having a lead content of between 0.5% and 50% by weight will advantageously simulate the spectral characteristics of terrestrial solar radiation. The glass is often known as lead glass, and sometimes referred to as flint glass. Lead glass is a glass that includes lead, or that a lead such as lead oxide is added to the glass mixture in order to adjust the mechanical, thermal, electrical or optical properties of the glass. In one example, lead glasses are glasses including potassium oxide, lead oxide and silicone dioxide as primary components. In a more particular example, the glasses can also include sodium oxide. Lead content described above is determined by the weight percent of the lead based on the total content of all materials in the glass formulation.

The amount of lead content of the glass in a suitable optical filter depends on the thickness of the glass used. A glass having a lead content of approximately 0.5% by weight should be approximately 10 mm thick to provide suitable filtering. A glass having a lead content of approximately 50% by weight need be only approximately 0.7 mm thick to provide suitable filtering. Those skilled in the art will now recognize that lead glass filters can be constructed over a wide range of lead contents but can also appreciate that lead glass filters can be too thin to be durable for use in accelerated weathering devices and to be too thick to be economical or practical for use in accelerated weathering devices. The range of lead content between 0.5% to 50% by weight is illustrated here as an example of a filter both durable and economical and practical for use in illuminators for typical accelerated weathering devices. In one example, the WG-320 had a lead content of about 30% by weight. The WG-320 glass is free of visible light absorbing components, meaning that the presence of such a component is undetectable with standard qualitative and quantitative analysis techniques. A suitable thickness of the WG-320 is about 1.3 mm. In the example for FIG. 6, the optical filter 352 is shown as a pane of WG-320 lead glass.

In addition, varying the thickness of the lead glass without varying the lead content by weight of the lead glass adjusts the spectral power distribution of illumination passed through the filter. Specifically, the thickness of the glass can be adjusted so that cut-on wavelength of illumination passing from the filter is the same as the cut-on wavelength for terrestrial solar illumination. For example, the cut-on wavelength for three optical filters constructed from WG-320 lead glass, each with different thicknesses was measured. The optical filters passed illumination from a xenon-arc lamp sold under the trade designation Oriel 66021, from Oriel Corp. of Stratford, Conn. For an optical filter that is 3 mm thick, the cut-on wavelength was approximately 298 nm; for an optical filter that is 2 mm thick, the cut-on wavelength was approximately 294 nm; and for an optical filter that is 1.3 mm thick, the cut-on wavelength was approximately 292 nm.

The above two criteria are met over a large range of power supplied to the light source. Typical weathering tests are conducted at 0.35 W/m² at 340 nm. In one example, the above two criteria were met with irradiance measured at 1.31 W/m² at 340 nm with a filter constructed from WG-320 lead glass having a wall thickness of 1.6 mm. The above two criteria are expected to be met over a larger range than described. The use of higher irradiance than typical with the present filter provides for faster test results. With related art filters, additional power can lead to faster unrealistic degradation or introduce or magnify errors in the simulation of terrestrial solar radiation.

In an optical filter assembly, optical filters not made from lead glass are made from a material that is ultraviolet transmissive. These filters do not substantially affect the advantageous simulation of terrestrial solar radiation. In one example, the ultraviolet transmissive optical filter has at least 60% light transmission at 250 nm and at 80% light transmission at 300 nm. (Other examples are contemplated.) The cut on wavelength for illumination passed through this optical filter assembly, including a lead glass optical filter and an ultra-violet transmissive optical filter, very closely approximates the cut on wavelength for the lead glass optical filter when used alone and is determined by the lead glass optical filter. One example of a material suitable for use in an ultraviolet transmissive optical filter is quartz glass having a thickness of 2 mm. Another example is a quartz glass with an infrared absorbing coating such as glass sold under the trade designation CIRA from Atlas Electric Devices of Chicago, Ill. having approximately the same thickness. Referring to FIG. 3, the inner filter 52 is constructed from a lead glass and the outer filter 54 is constructed from an ultraviolet transmissive glass such as quartz or quartz glass with an infrared absorbing coating. Alternatively, the inner filter 52 is constructed from the ultraviolet transmissive glass and the outer filter is constructed from lead glass.

Infrared absorbing coating on the quartz glass permits higher irradiance levels with a light source without a corresponding increase of the temperature of the product under test. One form of infrared control is with a water coolant. Another form of infrared control is the addition of an infrared absorbing material to the coolant. For example, cupric sulfates added to the water form an infrared absorbing coolant that begins absorbing light above 600 nm and matches the solar ultraviolet cut-on. Another form of infrared control is to use the glass with infrared absorbing coating in conjunction with the infrared absorbing coolant. Other examples of infrared control are known.

EXAMPLES

The following examples compare the spectral power distributions for weathering devices using various filters with that of hemispherical normal solar radiation measured in Phoenix, Ariz. at solar noon, on a perfectly clear day near the summer solstice. This was considered as "maximum daylight" where the amount of short wavelength UV radiation is at or near maximum. Spectral power distribution measurements in the weathering devices were made with a spectroradiometer commercially available from Optronics (Orlando, Fla.) under the trade designation OL754 with OL754-PMT optics head and OL752S integrating sphere. The spectroradiometer was calibrated with a standard tungsten halogen lamp (Optronics OL752-10E) with calibration traceable to National Institute for Standards and Technology (NIST). Spectral power distribution measurements were made from 250 to 400 nm at 2 nm increments.

The following examples include comparative examples labeled as Comparative Examples A–I. These examples describe commercially available articles for use in xenon-arcweathering devices. The following examples also describe examples of the present disclosure, which are labeled Examples 1–2. The following abbreviations are used in these examples.

| Abbreviation | Description |
| --- | --- |
| Q-Sun 3000 | Q-Sun 3000 Xenon Test Chamber equipped with standard daylight filters (Q-Panel Lab Products, Cleveland, Ohio) |
| Suntest | Heraeus Suntest table top xenon-arc device ((Heraeus DSET Laboratories, Phoenix, Arizona, now Atlas Electric Devices, Chicago, Illinois ("Atlas")) |
| Suprax | Trade designation for "daylight" xenon-arc filter supplied with Heraeus Suntest and Heraeus Xenotest 1200 CPS |
| Xenotest 1200 | Heraeus Xenotest 1200 CPS (Heraeus DSET Laboratories, Phoenix, Arizona, now Atlas) |
| Atlas Ci65A | Atlas Ci65A water cooled xenon-arc weathering device (Atlas) |
| Atlas Hi35 | Atlas Hi35 water cooled xenon-arc (Atlas) |
| Atlas Ci5000 | Atlas Ci5000 water cooled xenon-arc weathering device (Atlas) |
| CIRA | Coated Infrared Absorbing filter (Atlas) |
| Boro | Borosilicate "S" inner or outer filter for water cooled xenon-arc device (Atlas) |
| Soda lime | Soda lime glass filter for water cooled xenon-arc device(Atlas) |
| Oriel 66021 | Oriel model 66021 Universal Arc Lamp Housing with F1 Condenser equipped with Oriel 6271 1000 W xenon lamp, powered by Oriel 68820 IKW Arc Lamp Power Supply (Oriel Instruments, Stratford, Connecticut) |
| Soda lime glass | Flat plate of 1.5 mm thick soda lime glass (Industrial Glass Products, Los Angeles, California) |
| Hoya UV32 | Hoya UV32 (2.5 mm thick, Bes Optics, West Warwick, Rhode Island) |
| Tin Oxide glass | Tin oxide glass as described in U.S. Pat. No. 4,125,775 |
| Schott WG320 tube | Schott WG320 lead glass, Schott Glass Technologies, Inc., Dureya, Pennsylvania, formed into tube with wall thickness of 1.5 mm. |
| Quartz inner | Quartz inner filter for water cooled xenon-arc (Atlas) |
| Quartz outer | Quartz outer filter for water cooled xenon-arc manufactured by General Electric and cut to fit by Minnesota Mining and Manufacturing Company, St. Paul, Minnesota |
| Sylvania BS575 | Sylvania BS 575 SE HR metal halide lamp (Osram Sylvania, Photo Optics Division, Danvers, Massachusetts) |
| Schott WG320 sheet | Schott WG320 glass sheet, melt H0191, 2 mm thick Schott Glass Technologies, Inc., Dureya, Pennsylvania |

Table 1 shows the filters and light source used in each example and also the ratios of the irradiance below 290 nm and at 310 to the irradiance from 300–400 nm.

TABLE 1

| Example | Light source | Inner filter | Middle filter | Outer filter | Ratio of irradiance less than 290 nm to total irradiance from 300–400 nm | Ratio of irradiance at 310 nm to total irradiance from 300–400 nm |
| --- | --- | --- | --- | --- | --- | --- |
| Comp. A | Q-Sun 3000 | None | Q-Sun 3000 | None | 6.19E−06 | 0.0015 |
| Comp. B | Suntest | None | Suprax | None | 3.02E−04 | 0.0017 |
| Comp. C | Atlas Ci65A | Boro | None | Boro | 1.05E−04 | 0.0015 |
| Comp. D | Atlas Hi35 | Quartz | None | Boro | 1.76E−03 | 0.0029 |
| Comp. E | Xenotest 1200 | None | Suprax | None | 4.09E−04 | 0.0022 |
| Comp. F | Atlas Ci5000 | CIRA | None | Soda lime | 2.96E−04 | 0.0022 |

TABLE 1-continued

| Example | Light source | Inner filter | Middle filter | Outer filter | Ratio of irradiance less than 290 nm to total irradiance from 300–400 nm | Ratio of irradiance at 310 nm to total irradiance from 300–400 nm |
|---|---|---|---|---|---|---|
| Comp. G | Oriel 66021 | None | Hoya UV32 | None | 0.00E+00 | 0.0000 |
| Comp. H | Oriel 66021 | None | Soda lime glass | None | 0.00E+00 | 0.0004 |
| Comp. I | Oriel 66021 | None | Tin oxide glass | None | 0.00E+00 | 0.0006 |
| 1 | Atlas Ci65A | Quartz | Schott WG320 tube | Quartz | 0.00E+00 | 0.0025 |
| 2 | Sylvania BS575 | None | Schott WG320 sheet | None | 0.00E+00 | 0.0013 |

Figure 7:
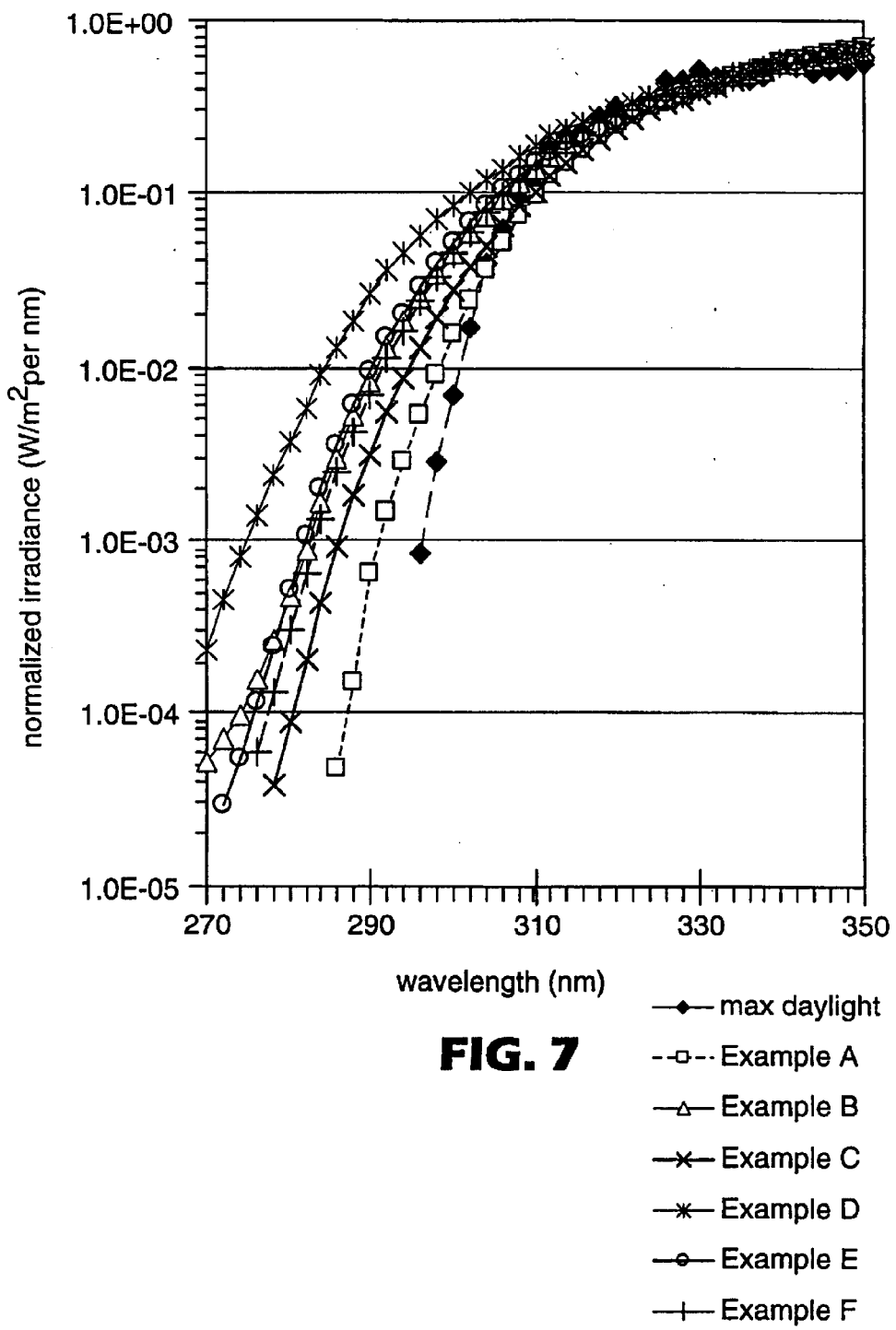
FIG. 7 shows a spectral power distribution of comparative examples and sunlight.

Comparative Examples A–F used filters commercially available in xenon-arc weathering devices. FIG. 7 shows the spectral power distribution for Comparative Examples A–F compared to maximum daylight from 270 to 350 nm. Spectral power distribution data in FIG. 7 and the other spectral power distribution graphs is normalized to 0.55 W/m$^2$ at 340 nm, which is a commonly used irradiance control point in laboratory accelerated weathering devices. The plot describes normalized irradiance in W/m$^2$ per nm as a function of wavelength in nm.

FIG. 7 shows that the spectral power distribution of the xenon-arc with the filters of Comparative Examples A–F contain significant amounts of short wavelength UV radiation below the cut-on of maximum daylight. This can lead to unrealistic degradation reactions in some materials.

Figure 8:
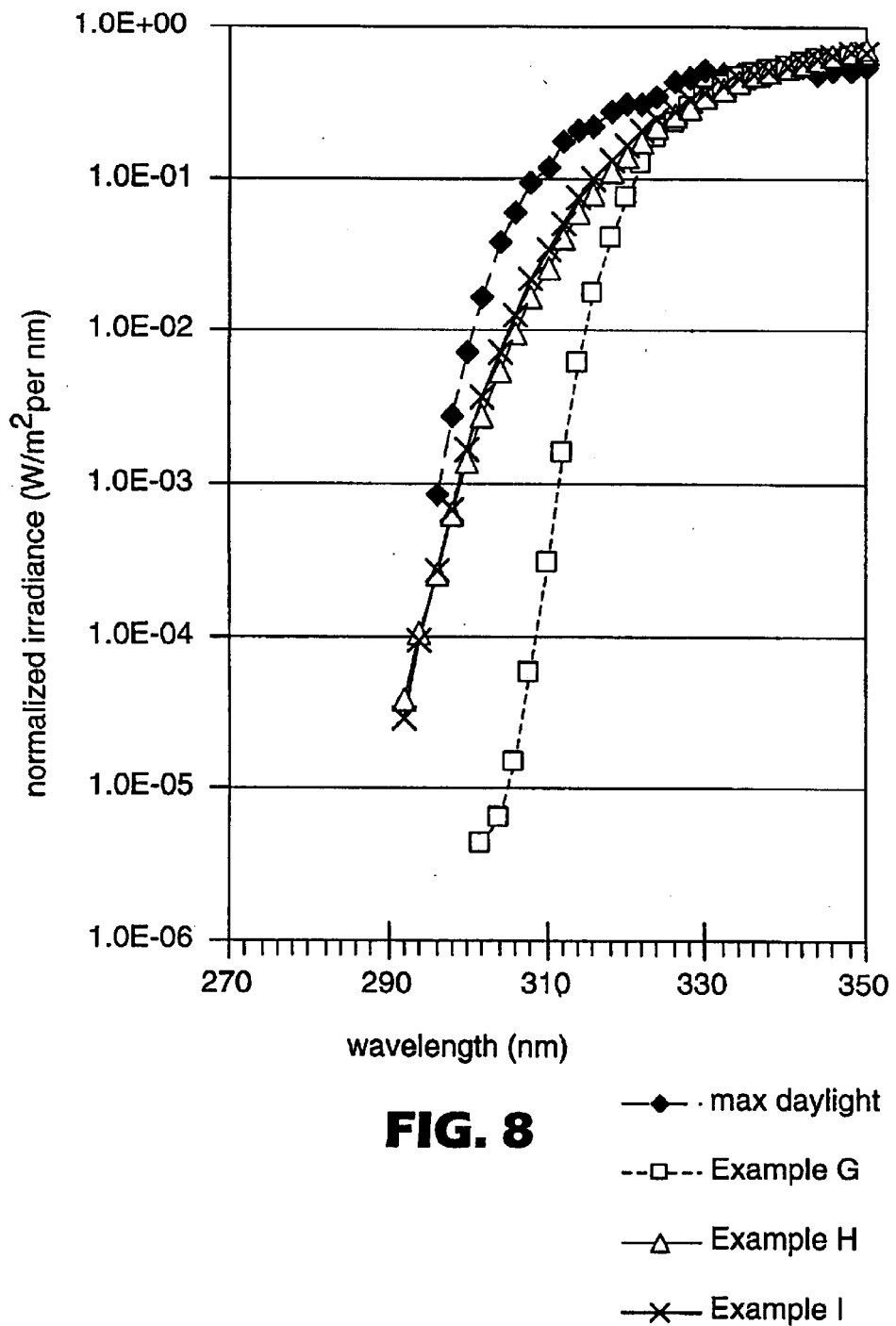
FIG. 8 shows a spectral power distribution of other comparative examples and sunlight.

Comparative Examples G–I used commercially available filters that remove short wavelength UV radiation below the solar cut on. FIG. 8 is a plot of the spectral power distribution of maximum daylight and Comparative Examples G–I with the irradiance data normalized to 0.55 W/m$^2$ at 340 nm. The plot describes normalized irradiance in W/m$^2$ per nm as a function of wavelength in nm.

FIG. 8 shows that when these filters are used to effectively remove short wavelength UV radiation from light sources used in laboratory accelerated weathering devices, too much of the radiation just above 300 nm that is present in solar radiation is also filtered out. This makes the spectral power distribution "weak" relative to maximum daylight and may cause undesirably long test times.

Figure 9:
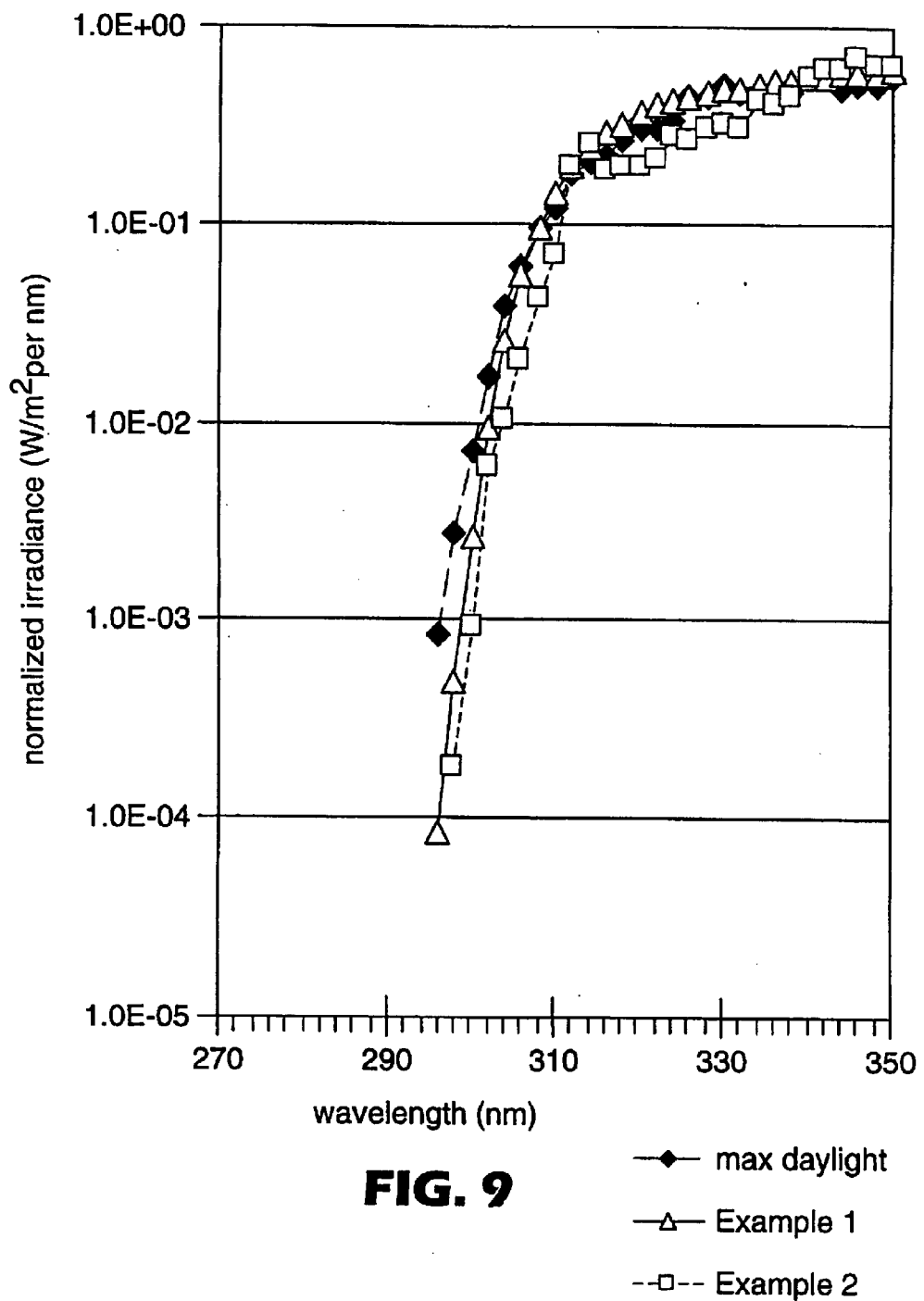
FIG. 9 shows a spectral power distribution of examples of the present disclosure and sunlight.

Examples 1 and 2 used the lead glass filters of the invention with a xenon-arc and a metal halide lamp. FIG. 9 is a plot of the spectral power distribution of maximum daylight and Examples 1 and 2 with the irradiance data normalized to 0.55 W/m$^2$ at 340 nm. The plot describes normalized irradiance in W/m$^2$ per nm as a function of wavelength in nm. FIG. 9 shows that when the filters of the invention were used, the short wavelength UV radiation of the laboratory accelerated light source was removed without unrealistically filtering out radiation above 300 nm that is present in maximum daylight. In FIG. 9, the cut-on of Examples 1 and 2 was shifted several nm to longer wavelength than for maximum daylight. A slight modification of the thickness or the lead content of the filter will provide a spectral power distribution that is essentially an exact match to that for maximum daylight.

The data in Table 1 and FIGS. 7–9 show that the use of the filters of the invention in laboratory accelerated weathering devices provides the capability to obtain test results in short time period that effectively simulate results obtained in actual outdoor exposures without unrealistic degradation reactions.

Various modifications and combinations of the embodiments disclosed will be apparent to those skilled in the art, and those modifications are intended to be within the scope of the invention as defined in the appended claims.

What is claimed:

1. An accelerated weathering device suitable for testing product samples, the accelerated weathering device comprising:
   a weathering fixture adapted to hold the product sample; and
   an illuminator disposed approximate the weathering fixture, the illuminator adapted to provide illumination to the product sample; wherein the illuminator includes a light source having spectral characteristics in at least the range of 200 nm to 400 nm; and
   an optical filter disposed proximate the light source the optical filter comprising:
      a lead glass filter of visible light absorbing components and having a thickness selected such that illumination passed through the lead glass has a first ratio of a first total irradiance for wavelengths shorter than 290 nm to a second total irradiance for wavelengths between 300 nm to 400 nm, wherein the first ratio is less than $2.0 \times 10^{-6}$; and
      a second ratio of an irradiance at 310nm to the second total irradiance, wherein the second ratio is at least $1.2 \times 10^{-3}$.

2. The accelerated weathering device of claim 1 wherein the thickness of the lead glass is selected to provide a cut-on wavelength for the illumination passed through the lead glass of between 290 nm to 300 nm.

3. The accelerated weathering device of claim 1 wherein the illumination from the light source includes a spectral component of at least 290 nm to 400 nm.

4. The accelerated weathering device of claim 1 wherein the illumination from the light source includes an irradiance of between 0.35 W/m$^2$ and 1.31 W/m$^2$ at 340 nm.

5. An accelerated weathering device suitable for testing product samples, the accelerated weathering device comprising:
   a weathering fixture adapted to hold the product sample; and an illuminator disposed approximate the weathering fixture, the illuminator adapted to provide illumination to the product sample; wherein the illuminator includes
a light source having spectral characteristics in at least the range of 200 nm to 400 nm; and
an optical filter disposed proximate the light source the optical filter comprising:
a lead glass free of visible light absorbing components and having a thickness selected such that the filtered illumination has
a cut-on wavelength of between 290 nm and 300 nm; and
a ratio of an irradiance at 310 nm to a total irradiance for wavelengths between 300 nm and 400 nm wherein the ratio is at least $1.2 \times 10^{-3}$.

6. An accelerated weathering device suitable for testing product samples, the accelerated weathering device comprising:
a weathering fixture adapted to hold the product sample; and
an illuminator disposed approximate the weathering fixture, the illuminator adapted to provide illumination to the product sample; wherein the illuminator includes
a light source having spectral characteristics in at least the range of 200 nm to 400 nm; and
an optical filter assembly for an accelerated weathering device, the accelerated weathering device having a light source providing illumination the optical filter assembly comprising:
an ultraviolet transmissive optical filter;
a lead glass free of visible light absorbing components operably coupled to the ultraviolet transmissive optical filter, the lead glass having a thickness selected such that illumination passed through the optical filter assembly has
a first ratio of a first total irradiance for wavelengths shorter than 290 nm to a second total irradiance for wavelengths between 300 nm to 400 nm, wherein the first ratio is less than $2.0 \times 10^{-6}$; and
a second ratio of an irradiance at 310 nm to the second total irradiance, wherein the second ratio is at least $1.2 \times 10^{-3}$.

7. The accelerated weathering device of claim 6 wherein in the ultraviolet transmissive optical filter provides at least 60% transmission of light at 250 nm and at least 80% transmission of light at 300 nm.

8. An accelerated weathering device suitable for testing product samples, the accelerated weathering device comprising:
a weathering fixture adapted to hold the product sample; and
an illuminator disposed approximate the weathering fixture, the illuminator adapted to provide illumination to the product sample;
wherein the illuminator includes
a light source having spectral characteristics in at least the range of 200 nm to 400 nm; and
an optical filter disposed proximate the light source, the optical filter comprising a glass free of visible light absorbing components and having a lead content of between 0.5% and 50% by weight.

9. The accelerated weathering device of claim 8 wherein the glass is cylindrical.

10. The accelerated weathering device of claim 8 wherein the glass has a thickness of between 0.7 mm and 10 mm.

11. The accelerated weathering device of claim 10 wherein the glass has a lead content of 30% by weight.

12. The accelerated weathering device of claim 8 wherein the optical filter comprises an ultraviolet transmissive optical filter operably coupled to the lead glass optical filter.

13. The accelerated weathering device of claim 12 wherein the ultraviolet transmissive optical filter is constructed from quartz glass.

14. The accelerated weathering device of claim 12 wherein the ultraviolet transmissive optical filter includes an infrared absorbing coating.

15. The accelerated weathering device of claim 12 including a plurality of ultraviolet transmissive optical filters.

16. The accelerated weathering device of claim 15 two ultraviolet transmissive optical filters.

17. The accelerated weathering device of claim 16 wherein the lead glass optical filter is disposed between the ultraviolet transmissive optical filters.

* * * * *

UNITED STATES PATENT AND TRADEMARK OFFICE
CERTIFICATE OF CORRECTION

PATENT NO.    : 6,906,857 B2
DATED         : June 14, 2005
INVENTOR(S)   : Fischer, Richard M. Jr.

It is certified that error appears in the above-identified patent and that said Letters Patent is hereby corrected as shown below:

Column 4,
Line 67, delete "$2.0 \times 10^6$" and insert -- $2.0 \times 10^{-6}$ --, therefor.

Column 10,
Line 41, after "source" insert -- , --.
Line 43, delete "filter" and insert -- free --, therefor.

Column 11,
Line 29, after "illumination" insert -- , --.

Column 12,
Line 2, delete "in" before "the".
Line 38, insert -- including -- before "two".

Signed and Sealed this

Twenty-ninth Day of November, 2005

JON W. DUDAS
*Director of the United States Patent and Trademark Office*